United States Patent [19]

Kudoh et al.

[11] 4,388,478

[45] Jun. 14, 1983

[54] PROCESS FOR THE ORTHO-ALKYLATION OF PHENOLIC COMPOUNDS

[75] Inventors: Akihide Kudoh; Motoo Kawamata; Kazushi Ohshima; Makoto Kotani, all of Yokohama; Takeshi Tsuda, Kanagawa; Fukuichi Aoki, Yokohama, all of Japan

[73] Assignee: Mitsui Toatsu Chemicals, Inc., Tokyo, Japan

[21] Appl. No.: 316,800

[22] Filed: Oct. 30, 1981

[30] Foreign Application Priority Data

Nov. 17, 1980 [JP] Japan ................................ 55-160686

[51] Int. Cl.$^3$ ............................................. C07C 37/16
[52] U.S. Cl. .................................. 568/804; 568/794
[58] Field of Search ..................... 568/804, 744, 794

[56] References Cited

U.S. PATENT DOCUMENTS

| | | | |
|---|---|---|---|
| 3,959,394 | 5/1976 | Tasake et al. | 568/804 |
| 3,971,832 | 7/1976 | Watanabe et al. | 568/804 |
| 4,227,023 | 10/1980 | Kawamata et al. | 568/804 |

FOREIGN PATENT DOCUMENTS

| | | | |
|---|---|---|---|
| 739786 | 3/1970 | Belgium | 568/804 |
| 47-18739 | 5/1972 | Japan | 568/804 |
| 49-18834 | 2/1974 | Japan | 568/804 |
| 54-32424 | 3/1979 | Japan | 568/804 |
| 200515 | 10/1967 | U.S.S.R. | 568/804 |

*Primary Examiner*—Werren B. Lone
*Attorney, Agent, or Firm*—Fisher, Christen & Sabol

[57] ABSTRACT

This invention relates to a process for the selective ortho-alkylation of a phenolic compound having at least one ortho-positioned hydrogen atom by catalytically reacting the phenolic compound with an alcohol in the vapor phase. In this process, the reaction of the phenolic compound with the alcohol is carried out at a temperature of from 300° to 550° C. in the presence of a catalyst containing manganese oxide and one or more additives selected from group (A) consisting of germanium oxide, tin oxide and lead oxide, or a catalyst containing manganese oxide, one or more additives selected from the aforesaid group (A), and one or more additives selected from group (B) consisting of alkali metal oxides and alkaline earth metal oxides. The catalyst used in this invention exhibits not only excellent catalytic activity in the selective ortho-alkylation of phenols, continuous stability of the activity, good shapeability and good mechanical strength but also effective utilization of alcohols.

6 Claims, No Drawings

PROCESS FOR THE ORTHO-ALKYLATION OF PHENOLIC COMPOUNDS

BACKGROUND OF THE INVENTION (A) Field of the Invention

This invention relates to a process for the selective alkylation of the unsubstituted ortho position or positions of phenolic compounds. More particularly, it relates to a process for carrying out the aforresaid alkylation with excellent results and long time stability in the presence of an improved catalyst containing manganese oxide as a main component.

(B) Description of the Prior Art

The preparation of 2,6-dimethylphenol, among other ortho-alkylated phenols, has heretofore been the subject of many studies because it is a raw material for the manufacture of polyphenyleneether having a wide range of utility as a heat resisting resin.

Currently, a process for the ortho-alkylation of phenols is in industrial use which involves the vapor phase reaction of a phenol with an alcohol in the presence of an acidic solid catalyst such as alumina. However, in this process, the selectivity in the site of alkylation is insufficient. That is, not only the ortho-positions thereof are subject to alkylation, so that a complicated procedure for the separation and purification of ortho-alkylated reaction products is required.

Another industrial process for the ortho-alkylation of phenol is based on vapor phase reaction in the presence of a magnesium oxide catalyst. However, this catalyst has inherently low activity and requires high temperatures of 475° C. or higher, practically 500° C. or higher, to achieve sufficient reaction.

Moreover, the life of the catalyst is not long enough, so the regeneration procedure must be required in a relatively short period of time for practical use.

In order to solve these problems, there have been proposed many kinds of catalysts, especially those comprising mainly manganese oxide. For example, U.S. Pat. No. 3,971,832 discloses a catalyst comprising mainly trimanganese tetraoxide, Japanese Patent Publication No. 11100/1976 discloses a manganese oxide catalyst which has magnesium oxide or selenium oxide added to it, and Japanese Patent Laid-open No. 32425/1979 discloses the addition of silicon dioxide.

A catalyst comprising mainly manganese oxide has excellent selectivity of ortho-alkylation and high activity; however, the present inventors propose a catalyst disclosed in the U.S. Pat. No. 4,227,023 which comprises mixed oxide of manganese and silicon and one or more additives selected from alkaline earth metals for improving physical strength of the catalyst, and a catalyst disclosed in Japanese Patent Laid-Open No. 76830/1980 which comprises manganese oxide and is treated with alkali metal compound for preventing the depositing of oxygen containing hydrocarbon species onto the surface of the catalyst and for prolonging the service life of the catalyst.

The catalysts exhibit good characteristics as practical catalysts; however, they are still insufficient in effective utilization of alcohols.

The present inventors have undertaken extensive studies for the purpose of overcoming the above mentioned disadvantage in the aforesaid prior art process, and have discovered that mixed metal oxide catalysts with one or more additives included selected from group (A) consisting of germanium oxide, tin oxide and lead oxide are excellent for the improvement of effective utilization of alcohols.

BRIEF SUMMARY OF THE INVENTION

It is an object of the present invention to provide an improved process for the selective ortho-alkylation of a phenolic compound having at least one ortho-positioned hydrogen atom by catalytically reacting the phenolic compound with an alcohol in the vapor phase.

It is another object of the present invention to provide a catalyst which is available in carrying out the aforesaid selective ortho-alkylation reaction, the catalyst exhibiting not only enhanced catalytic activity and excellent characteristics required for industrial catalysts, such as good shapability and high mechanical strength, but also are excellent for improving the effective utilization of alcohols.

These and other objects of the present invention will become more apparent from the following detailed description and examples.

According to the present invention, there is provided a process for the selective ortho-alkylation of a phenolic compound having at least one ortho-positioned hydrogen atom by catalytically reacting the phenolic compound with an alcohol in the vapor phase wherein the improvement comprises carrying out the reaction in the presence of a catalyst containing manganese oxide and one or more additives selected from group (A) consisting of germanium oxide, tin oxide and lead oxide, or a catalyst containing manganese oxide, one or more additives selected from group (A) consisting of germanium oxide, tin oxide and lead oxide, and one or more additives selected from group (B) consisting of alkali metal oxides and alkaline earth metal oxides.

DETAILED DESCRIPTION OF THE PREFERRED EMBODIMENTS

The phenolic compound which is used in the practice of the invention is one having a hydrogen atom in at least one of the ortho positions and can be represented by the formula

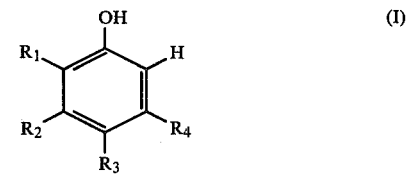

where $R_1$, $R_2$, $R_3$ and $R_4$ independently represent hydrogen atoms or aliphatic hydrocarbon groups such as methyl, ethyl, n-propyl, iso-propyl, n-butyl, iso-butyl and tert-butyl groups.

Specific examples of the phenolic compound include phenol; o-, m- and p-cresols; 2,3-, 2,4-, 2,5-, 3,4- and 3,5-xylenols; trimethylphenols; tetramethylphenols; n- and iso-propylphenols; n-, iso- and tert-butylphenols; and the like. In addition, phenolic compounds having at least two different alkyl substituent groups on the same aromatic ring are also usable.

The alcohol which is used in the practice of the invention is a saturated aliphatic alcohol having from 1 to 4 carbon atoms. Specific examples of the alcohol include methyl alcohol, ethyl alcohol, isopropyl alcohol, n-propyl alcohol, n-butyl alcohol, isobutyl alcohol, tert-butyl alcohol, and the like.

The catalyst which is used in the process of the invention contains manganese oxide and one or more additives selected from group (A) consisting of germanium oxide, tin oxide and lead oxide. Said additives selected from group (A) are suitably present in such proportion as to provide a metal atomic ratio of manganese oxide to said additives ranging from 100:0.1 to 100:50 and preferably from 100:0.3 to 100:30.

When the catalyst further contains one or more additives selected from group (B) consisting of alkali metal oxides and alkaline earth metal oxides, said additives are present in such proportion as to provide an atomic ratio of manganese to alkaline earth metals ranging from 100:0.01 to 100:30 and preferably 100:0.05 to 100:20, and an atomic ratio of manganese to alkali metals ranging from $100:10^{-4}$ to 100:5 and preferably from $100:10^{-3}$ to 100:1.

The role of an alkaline metal oxide in this invention is one of mainly providing moldability as a practical catalyst, in other words, the moldability of the catalyst is improved while maintaining the selectivity of obtaining ortho-alkylated phenols based on phenols and alcohols at high level.

On the other hand, the role of an alkali metal oxide is mainly one of suppressing the decomposition of alcohols, which is useless for objective reaction, and reducing the deposition of hydrocarbons produced by reaction of organic materials onto the surface of the catalyst and prolonging the service life of the catalyst.

As raw materials of various metal oxides which are used in this invention, derivatives of each metal, such as hydroxides, carbonates, salt of various mineral acids, salt of organic acids, in some cases sulfide, hydride and the like, may be used.

A number of methods are available for the preparation of the catalyst. For example, it may be prepared either by adding a small amount of water to a mixture of various compounds as described above and blending the mixture well in a kneader or mixer, or by adding a suitable basic component to an aqueous solution of various raw materials and obtaining the coprecipitated insoluble products. It is also possible to form a mixture of some component first and then the remaining components are added by dipping or mixing. Usually, the resulting catalyst is dried at a temperature below 150° C., and suitable additives or processing aids are added such as polyvinyl alcohol, microcrystallite cellulose, and the like, if desired, and formed into any desired shape by a suitable technique such as extrusion, compression molding, vibration, rolling, or the like, and then calcined to make it ready for use.

In carrying out the process of the invention, a phenolic compound and an alcohol are mixed in a molar ratio ranging from 1:1 to 1:15 and preferably from 1:1 to 1:6. Prior to being fed the reactants to the reaction zone, these starting materials may be diluted with a suitable inert gas such as nitrogen or carbon dioxide to make the reaction proceed smoothly. Furthermore, it is also effective to introduce a small amount of water with the reactants into the reaction zone. The presence of such water serves not only to prolong the service life of the catalyst but also to suppress any undesirable decomposition of the alcohol.

The process of the invention is carried out at a temperature of from 300° C. to 550° C. and preferably from 350° to 500° C. If the reaction temperature is higher, the selectivity for ortho-alkylation is reduced and the formation of various high-boiling products is increased. On the other hand, if the reaction temperature is lower, the conversion of the reactants is insufficient for the practical use, as a result, great amounts of unreacted starting materials or intermediate products must be recovered and recycled.

The reactants are preferably fed to the reaction zone at a liquid space velocity of from 0.01 to 12 per hour. Generally speaking, greater liquid space velocities are suitably used for the reactions of higher temperature, and vice versa. The reaction may be carried out under a pressure higher or lower than atmospheric pressure. The reaction may be carried out according to any of the fixed bed, fluidized bed, and moving bed processes.

The present invention is further illustrated by the following examples.

EXAMPLE 1

Five hundred g of manganese nitrate hexahydrate was heated to 40° C. and diluted with water up to 2,500 ml of solution. Then aqueous ammonia was added and a precipitate was formed. This precipitate of manganese hydroxide was washed sufficiently with water, filtered and then dried at 130° C. for 8 hours.

This dried filter cake and 3.2 g of germanium dioxide white powder were well mixed together by a grinding mixer including the addition of a suitable amount of water and then dried again at 130° C. for 8 hours. Next, it was ground and molded by compression into cylindrical pellets in a known manner, having a diameter of 4.8 mm and a height of 3.2 mm, and then burnt at 500° C., whereby a catalyst consisting of manganese oxide and germanium oxide was prepared. The catalyst was composed of a Mn:Ge atomic ratio of 100:2.5 by elemental analysis.

One hundred g of the catalyst was packed into a stainless steel tubular reactor having an internal diameter of 21 mm.

Alkylation of phenol with methanol was carried out according to following procedure.

A mixture of phenol and methanol (in a molar ratio of 1:5) was gasified passing through the carburetor controlled at a temperature of 230° C., and then introduced into the reactor, the internal temperature of which was kept at 430° C., at a rate of 35 g per hour.

The reaction products was analyzed by gas chromatography. The results are summarized in Table 1. The rate of methanol effective utilization is calculated according to the following formula.

Rate of methanol effective utilization (%) =

$$\frac{\text{Produced o-cresol (mol)} + \text{Produced 2,6-xylenol (mol)} \times 2}{\text{Reacted methanol (mol)}} \times 100$$

EXAMPLE 2

A catalyst consisting of manganese oxide and tin oxide was prepared in the same manner as described in Example 1 except that the germanium dioxide was replaced by white powder of tin oxalate. (with a Mn:Sn atomic ratio of 100:4.9)

Alkylation of phenol with methanol was carried out in the same manner as described in Example 1 except that the reaction temperature was changed to 415° C. The results are shown in Table 1.

EXAMPLE 3

A catalyst consisting of manganese oxide, tin oxide and calcium oxide were prepared as described in Example 2 except that the white powder of calcium hydroxide is further added with tin oxalate. (with a Mn:Sn:Ca atomic ratio of 100:4.8:1.1)

Alkylation of phenol methanol was carried out in the same manner as described in Example 1 except that the reaction temperature was changed to 410° C. The results are shown in Table 1. After about 350 hours continuation of reaction, the pelletized catalyst was removed from the tubular reactor, there was practically no damage to the shape of the pellets.

EXAMPLE 4

One hundred g of pelletized catalyst prepared in Example 1 was dipped into 0.01 N of potassium hydroxide aqueous solution, whereby a catalyst treated with potassium was prepared. The catalyst was composed of a Mn:Ge:K atomic ratio of 100:2.5:0.002 by elemental analysis.

Alkylation of phenol with methanol was carried out in the same conditions as described in Example 1. The results are shown in Table 1.

EXAMPLE 5

A catalyst treated with potassium was prepared as described in Example 4 using the pelletized catalyst which was prepared in Example 3. (with a Mn:Sn:Ca:K atomic ratio of 100:4.8:1.1:0.003)

Alkylation of phenol with methanol was carried out under the same conditions as descirbed in Example 3. The results are shown in Table 1.

EXAMPLE 6

A catalyst consisting of manganese oxide and lead oxide was prepared in the same manner as described in Example 1 except that the germanium dioxide was replaced by blackish brown powder of lead dioxide. (with a Mn:Pb atomic ratio of 100:1.1)

Alkylation of phenol with methanol was carried out in the same manner as described in Example 1 except that the reaction temperature was changed into 418° C. The results are shown in Table 1.

EXAMPLE 7

One hundred g of catalyst which was prepared in Example 6 was dipped into 0.01 N of cesium nitrate aqueous solution, whereby a catalyst treated with cesium was prepared. The catalyst was composed of a Mn:Pb:Cs atomic ratio of 100:1.1:0.003 by elemental analysis.

Alkylation of phenol methanol was carried out in the same conditions as described in Example 6. The results are shown in Table 1.

TABLE 1

| Example No. | Composition of Catalyst (Atomic Ratio) | Hours after Initiation of Reaction | Phenols in Products (mol %) | | | | Rate of Methanol Effective Utilization (%) |
|---|---|---|---|---|---|---|---|
| | | | Phenol | o-Cresol | 2,6-Xylenol | 2,4,6-Trimethylphenyl | |
| 1 | Mn:Ge = 100:2.5 | 10 | 0.9 | 10.3 | 85.1 | 2.1 | 62 |
| | | 100 | 2.0 | 15.1 | 80.0 | 1.9 | 60 |
| 2 | Mn:Sn = 100:4.9 | 10 | 1.5 | 8.2 | 89.3 | 0.9 | 68 |
| | | 100 | 4.1 | 13.5 | 80.0 | 0.5 | 64 |
| 3 | Mn:Sn:Ca = 100:4.8:1.1 | 50 | 0.5 | 4.2 | 92.3 | 2.6 | 59 |
| | | 150 | 1.1 | 6.9 | 90.4 | 1.5 | 55 |
| | | 300 | 3.2 | 9.8 | 85.9 | 1.0 | 55 |
| 4 | Mn:Ge:K = 100:2.5:0.002 | 50 | 0.8 | 9.9 | 86.3 | 2.0 | 60 |
| | | 200 | 1.1 | 10.3 | 85.9 | 1.8 | 60 |
| | | 400 | 1.9 | 13.9 | 82.0 | 1.5 | 59 |
| 5 | Mn:Sn:Ca:K = 100:4.8:1.1:0.003 | 50 | 0.4 | 4.0 | 93.0 | 2.0 | 60 |
| | | 200 | 0.9 | 5.0 | 92.5 | 1.5 | 58 |
| | | 450 | 2.5 | 8.0 | 88.1 | 1.1 | 56 |
| 6 | Mn:Pb = 100:1.1 | 10 | 2.2 | 15.0 | 80.5 | 2.0 | 71 |
| | | 50 | 3.0 | 20.3 | 74.6 | 1.9 | 70 |
| 7 | Mn:Pb:Cs = 100:1.1:0.003 | 10 | 1.7 | 13.0 | 82.6 | 2.5 | 68 |
| | | 50 | 2.9 | 16.5 | 78.1 | 2.2 | 65 |

COMPARATIVE EXAMPLE

The dried precipitate of manganese hydroxide which was prepared in Example 1, was molded by compression into cylindrical pellets having a diameter of 4.8 mm and a height of 3.2 mm and then burnt at 500° C. whereby a catalyst consisting of manganese oxide alone was prepared.

Alkylation of phenol with methanol was carried out in the same manner as described in Example 1 except that the reaction temperature was changed to 425° C. The results are shown in Table 2.

TABLE 2

| Phenols in Products (mol %) | | | | Rate of Methanol Effective Utilization (%) | Note |
|---|---|---|---|---|---|
| Phenol | o-Cresol | 2,6-Xylenol | 2,4,6-trimethyl-phenol | | |
| 0.9 | 6.5 | 92.0 | 0.5 | 60 | 1 hour after initiation of reaction |
| 2.9 | 15.0 | 81.5 | 0.4 | 55 | 20 hours after initiation of reaction |
| 9.5 | 21.9 | 67.9 | 0.4 | 50 | 70 hours after initiation of reaction The shape of almost all of the pelletized catalyst was damaged at 100 hours after initiation of reaction. |

What is claimed is:

1. In a process for the selective ortho-alkylation of a phenolic compound having at least one ortho-positioned hydrogen atom by catalytically reacting the phenolic compound with a saturated aliphatic alcohol having from 1 to 4 carbon atoms in the vapor phase at a temperature of from 300° C. to 550° C., the improvement of which comprises carrying out the reaction in the presence of a catalyst containing manganese oxide and one or more additives selected from group (A) consisting of germanium oxide, tin oxide and lead oxide, said additives selected from the group (A) are present in such proportion as to provide an atomic ratio of manganese to said additives ranging from 100:0.1 to 100:50.

2. A process as claimed in claim 1 wherein the catalyst further contains one or more additives selected from group (B) consisting of alkali metal oxides and alkaline earth metal oxides, said additives selected from the group (B) are present in such proportion as to provide an atomic ratio of manganese oxide to alkaline earth metals ranging from 100:0.01 to 100:30 and an atomic ratio of manganese to alkali metals ranging from 100:1³¹ ⁴ to 100:5.

3. A process as claimed in claim 1 or 2 wherein the phenolic compound and the alcohol are fed to the reaction zone in a molar ratio ranging from 1:1 to 1:15.

4. A process as claimed in claim 1 or 2 wherein the phenolic compound and the alcohol are fed to the reaction zone at a liquid space velocity of from 0.01 to 12 per hour.

5. A process as claimed in claim 1 or 2 wherein the phenolic compound having at least one ortho-positioned hydrogen atom is phenol and/or o-cresol.

6. A process as claimed in claim 1 or 2 wherein the alcohol is methyl alcohol.

* * * * *